(12) United States Patent
Grote et al.

(10) Patent No.: US 7,803,756 B2
(45) Date of Patent: *Sep. 28, 2010

(54) ANTIMICROBIAL PEPTIDES DERIVED FROM CAP18

(75) Inventors: Johannes Jakobus Grote, Zoeterwoude (NL); Jan Wouter Drijfhout, Leiden (NL); Pieter Sicco Hiemstra, Leiden (NL); Marcel Jan Vonk, Zoeterwoude (NL); Maartje Johanna Nell, Leiden (NL); Guido Vincent Bloemberg, Leiden (NL)

(73) Assignees: Octoplus Technologies B.V., Leiden (NL); Academisch Ziekenhuis Leiden, Leiden (NL)

( * ) Notice: Subject to any disclaimer, the term of this patent is extended or adjusted under 35 U.S.C. 154(b) by 309 days.

This patent is subject to a terminal disclaimer.

(21) Appl. No.: 11/658,415

(22) PCT Filed: Jul. 26, 2005

(86) PCT No.: PCT/NL2005/000545

§ 371 (c)(1),
(2), (4) Date: Feb. 19, 2008

(87) PCT Pub. No.: WO2006/011792

PCT Pub. Date: Feb. 2, 2006

(65) Prior Publication Data

US 2008/0249022 A1 Oct. 9, 2008

(30) Foreign Application Priority Data

Jul. 28, 2004 (EP) .................................. 04077175

(51) Int. Cl.
*C07K 14/00* (2006.01)
(52) U.S. Cl. .......................................... 514/2; 530/350
(58) Field of Classification Search ........................ None
See application file for complete search history.

(56) References Cited

U.S. PATENT DOCUMENTS 6,040,291 A * 3/2000 Hirata .......................... 514/12

FOREIGN PATENT DOCUMENTS

| EP | 0 955 312 | 11/1999 |
|---|---|---|
| WO | WO-2004/067563 | 8/2004 |
| WO | WO-2005/040192 | 5/2005 |

OTHER PUBLICATIONS

Gutsmann et al., Biophysical Journal (2001) 80:2935-2945.
International Search Report for PCT/NL2005/000545, mailed on Jan. 26, 2006, 3 pages.
Kirikae et al., Infection and Immunity, American Society for Microbiology (1998) 66(5):1861-1868.
Nagaoka et al., Clinical and Diagnostic Laboratory Immunology, American Society for Microbiology (2002) 9(5):972-982.
Turner et al., Antimicrobial Agents and Chemotherapy, American Society for Microbiology (1998) 42(9):2206-2214.

* cited by examiner

*Primary Examiner*—Karen Cochrane Carlson
(74) *Attorney, Agent, or Firm*—Morrison & Foerster LLP

(57) ABSTRACT

The invention provides methods to exert antimicrobial effects in prophylactic or therapeutic treatment of bacterial or fungal infections employing polypeptides that have affinity to microbial and fungal toxins.

Figure 1:
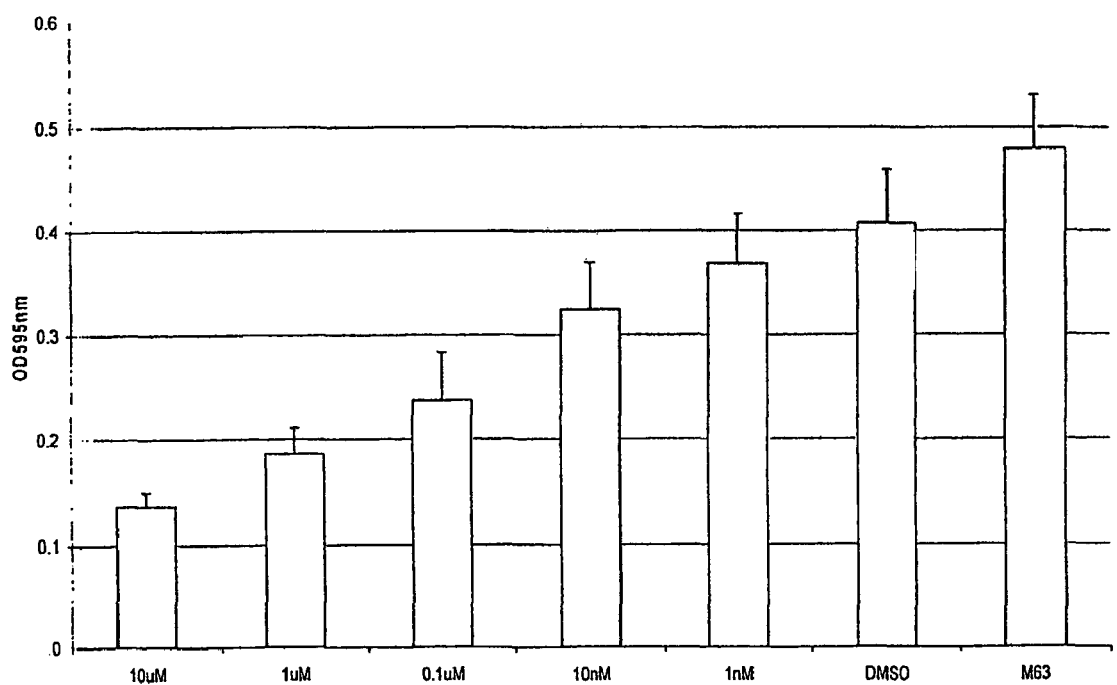

30 Claims, 1 Drawing Sheet

# ANTIMICROBIAL PEPTIDES DERIVED FROM CAP18

CROSS-REFERENCE TO RELATED APPLICATIONS

This application is the national phase of PCT application PCT/NL2005/000545 having an international filing date of 26 Jul. 2005, which claims priority from European application 04077175.0 filed 28 Jul. 2004. The contents of these documents are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 313632003400Seqlist.txt | Feb. 14, 2008 | 2,140 bytes |

FIELD OF THE INVENTION

The invention relates to antimicrobial compounds which inhibit or kill microorganisms including gram-negative bacteria and fungi. In addition, the compounds have affinity for toxins and especially for fungal and bacterial toxins such as lipopolysaccharide (LPS) or lipoteichoic acid (LTA), and which can inhibit or neutralize such toxins. Furthermore, the present invention relates to the therapeutic and diagnostic use of the compounds, and to pharmaceutical compositions comprising the compounds, and methods for their administration.

BACKGROUND OF THE INVENTION

Modern pharmacotherapy has been extremely successful in fighting bacterial infections, which used to be one of the prime causes of premature death until the middle of the last century. More recently, however, growing concerns over the wide-spread use of highly effective antibiotics have arisen because of the steady increase of bacterial resistance. In fact, over the past 25 years, antibiotic resistance—especially multiple resistance to a broad range of antibiotic compounds—has increased in virtually every species of bacteria examined. It is presently believed that the antibacterial agents of the most advanced type, which are unaffected by common resistance mechanisms, are the compounds which use appears to select for multidrug-resistant mutants.

Based on this development, experts recommend to use antibiotics far more restrictively than in the past, both in agriculture and in human medicine. For instance, minor infections—especially those which are not even typically caused by bacteria, such as the common cold—should not be treated with antibiotics, which should rather be reserved for more serious conditions. Furthermore, it is necessary to develop novel compounds for treating bacterial infections with completely different types of pharmacological activity, preferably with some activity which is independent from bacterial resistance to common antibiotics.

One of the conditions in which the widespread use of antibiotics has been discussed controversially is otitis media, either in its acute form or in its chronic state. It has been shown that the number of patients with otitis media with effusion (OME), i.e. a type of otitis characterized by the presence of fluid in the middle ear without the symptoms of an acute infection, has increased dramatically after the introduction of antibiotic therapy for early acute otitis media (AOM), suggesting that the antibiotics themselves play a part in OME (Lim et al., Laryngoscope 92, 278-286, 1982). It is believed that antibiotics like penicillin interfere with the development of local immune responses, such as with the production of local IgM in the middle ear (Howie et al., Ann. Otol. Rhinol. Laryngol. 85 Suppl. 25, 18-19, 1976). Another disadvantage of conventional antibiotic therapy is that the bacteria are killed, but their toxins are still active.

It has been suggested that, for the treatment of these and other conditions resulting from bacterial or fungal infection, it may be advantageous to use compounds which do not kill the microorganisms or germs themselves, but rather neutralize their toxins and allow the natural host defence mechanisms to control the spread of the infection (Nell, The Role of Endotoxin in the Pathogenesis of Otitis Media With Effusion, PhD Thesis, Leiden, 1999). At the same time, this strategy would support the rapid restoration of impaired mucosal functions.

A major role among microbial toxins, such as fungal toxins and especially bacterial toxins, involved in a number of infectious conditions such as otitis is played by endotoxins, a group of lipopolysaccharides (LPS) found in the cell wall of gram-negative bacteria, consisting of a polysaccharide conjugated with a highly toxic lipid moiety, lipid A. One of the recent therapeutic approaches to treat OME is to administer compounds that neutralize endotoxin, or LPS (Nell, ibid.).

Various compounds capable of neutralizing endotoxin, or LPS, are presently known. For instance, several anti-endotoxin antibodies have been developed, such as HA-1A and E5, a human and a mural monoclonal IgM antibody, respectively. These antibodies have been shown to improve survival rates of patients with some severe conditions such as septic shock (Ziegler et al., New Engl. J. Med. 324, 429-436, 1991). However, their activity and specificity is considered unsatisfactory.

Another group of substances active against endotoxin is derived from a human endogenous protein termed bacterial permeability-increasing protein (BPI), which is stored in the azurophilic granules of neutrophils (Gazzano-Santoro et al., Infection and Immunity 60:11, 4754-4761, 1992). BPI, which is a strongly cationic protein, not only neutralizes free endotoxins, but also inhibits or kills bacteria cells per se by increasing the permeability of their outer membranes. BPI is indeed a potent, natural antibiotic, induced by the presence of LPS and some other triggers including tumor necrosis factor (TNF). However, most of its activity is associated with the immune cells synthesizing it, i.e. polymorphonuclear macrophages.

Several recombinant proteins derived from BPI have also been developed, such as $rBPI_{23}$ (Kohn et al., 1993) and $rBPI_{21}$ (Horwitz et al., 1996), which largely represent the N-terminal portions of BPI with molecular weights of 23 and 21 kDa, respectively. The use of BPI and BPI-derived compounds in the treatment of OME has, e.g., been described in WO-A-00/71149.

Another family of natural compounds with antimicrobial activity are the cathelicidins, a class of peptides produced by respiratory epithelial cells, alveolar macrophages, and other tissues. In their native forms, these compounds are linear, α-helical, cysteine-free peptides or proteins. Cathelicidins are cationic and comprise a highly conserved signal sequence and pro-region, cathelin. However, their C-terminal domain encoding the mature peptide shows substantial heterogeneity. The peptides may have 12 to 80 amino acids.

The most prominent human cathelicidin is an 18 kDa cationic antimicrobial protein, CAP18. The 37 C-terminal amino acids of CAP 18, i.e. peptide LL-37, represent a domain responsible for the high affinity and neutralizing capacity for LPS (Sawa et al., Antimicr. Agents Chemother. 42:12, 3269-3275, 1998). Several truncated peptides derived from CAP18 or LL-37 have been developed and tested, such as those disclosed by Sawa (Sawa et al., ibid.), Gutsmann (Gutsmann et al., Biophys. J. 2935-2945, 2001), and in U.S. Pat. No. 6,040,291. In general, relatively small peptides are preferred over proteins such as CAP 18 as lead candidates for therapeutical compounds for several reasons. Firstly, they can more easily be optimized, adapted, and modified to conserve or augment their desired activity and specificity. Secondly, they are easier to obtain or synthesize, and therefore more accessible. Thirdly, they are easier to formulate and deliver, as proteins are often unstable and not bioavailable after non-parenteral administration.

The co-pending International Patent Application PCT/NL2004/00060, which is incorporated herein by reference, discloses peptidic compounds which have affinity to microbial and fungal toxins such as LPS and LTA. The compounds comprise an amino acid sequence $X_1KEFX_2RIVX_3RIKX_4FLRX_5LVX_6$ (SEQ ID NO:1) (herein-below, also referred to as core amino acid sequence), wherein $X_1$ represents the N-terminal part of the sequence, $X_2$ is K or E, $X_3$ is Q or E, $X_4$ is D or R, $X_5$ is N or E, and $X_6$ represents the C-terminal part; and wherein one or more of the amino acids of the core sequence may be derivatized. The sequence is further characterised in that the N-terminal part is acetylated, and/or that the C-terminal part is amidated, and/or that the amino acid sequence is different from $X_1KEFKRIVQRIKDFLRNLVX_6$ (SEQ ID NO:2).

Said patent application further describes methods for the preparation of such compounds. The methods include the chemical and enzymatic ligation of amino acids monomers or oligomers to assemble the compounds. They also include the expression of nucleic acid sequences encoding the compounds in host cells, using a vector for transfecting the host cells with the nucleic acid sequences. A method for the preparation of a compound according to any one of the previous claims, wherein amino acid monomers, amino acid oligomers, or mono- or oligomers of amino acid analogues or mimetics are assembled by chemical or enzymatic ligation, which is performed in a liquid phase and/or at the interface to a functionalized solid phase.

These compounds have been found to be useful in the management of conditions associated with or resulting from infections. It was suggested that they may be therapeutically more useful than conventional antibiotics in the treatment of certain chronic infections, such as otitis media. However, in the case of severe acute infections, effective control of microbial growth still is considered indispensable, which is achieved by the administration of antibiotics.

OBJECTS OF THE INVENTION

Despite the efforts in the prior art, there is a need for improvements in the prophylactic respectively therapeutic treatment of infectious diseases, including systemic or local bacterial and fungal infections. One of the objects of the invention is to provide new therapies which are safe, effective and which lead to an effective control of infective microorganisms. It is another object to provide therapies which do not easily lead to microbial resistance. Furthermore, it is an object of the invention to provide therapies which also reduce the undesirable effects of conventional antimicrobial therapy, such as the toxic effects of the microbial toxins which are released when microorganisms are killed by antimicrobial compounds in the body.

These and other objects of the present invention will become clear on the basis of the following description.

SUMMARY OF THE INVENTION

In a first aspect, the present invention provides the use of a peptidic compound for the manufacture of a medicament for the prevention or therapeutic treatment of a bacterial or fungal infection of a mammal, wherein the compound comprises an amino acid sequence $X_1KEFX_2RIVX_3RIKX_4FLRX_5LVX_6$ (SEQ ID NO:1), wherein $X_1$ represents the N-terminal part of the sequence, $X_2$ is K or E, $X_3$ is Q or E, $X_4$ is D or R, $X_5$ is N or E, $X_6$ represents the C-terminal part. One or more of the amino acids of the core sequence are optionally derivatized. Furthermore, the N-terminal part is acetylated, and/or the C-terminal part is amidated, and/or the amino acid sequence is different from the native amino acid sequence $X_1KEFKRIVQRIKDFLRNLVX_6$ (SEQ ID NO:2).

Such compounds were surprisingly found to have not only affinity to lipopolysaccharides (LPS) or lipoteichoic acid (LTA), but also direct antimicrobial, or microbicidal, activity. That is, these compounds can be used in the manufacture of medicament that kills bacteria and fungi. The compounds have bactericidal and fungicidal activity. By virtue of this activity, the compounds can be therapeutically used as antibiotics, even in diseases and conditions which could not be treated with compounds capable of neutralising microbial toxins alone. Examples of such diseases are acute bacterial or fungal infections, such as septic shock, acute infections of the eye(s), liver, kidney(s), lungs, bronchi, nasal or frontal sinus, ear(s), vagina, urethra, skin, central nervous system, cardiac muscle, spleen, and other organs and tissues.

In a further aspect, the invention relates to medicaments which are suitable for the prevention and/or treatment of diseases and conditions resembling bacterial or fungal infections, or being associated with bacterial or fungal infections.

Further aspects of the invention will be set forth in the detailed description below and in the appending claims.

DETAILED DESCRIPTION OF THE INVENTION

It was surprisingly found that the peptidic compounds disclosed in the co-pending International Patent Application PCT/NL2004/00060 do not only neutralise bacterial and fungal toxins such as lipopolysaccharides (LPS) and lipoteichoic acid (LTA), but also have a significant antimicrobial activity. These compounds comprise the core amino acid sequence $X_1KEFX_2RIVX_3RIKX_4FLRX_5LVX_6$ (SEQ ID NO:1), wherein $X_1$ represents the N-terminal part of the sequence, $X_2$ is K or E, $X_3$ is Q or E, $X_4$ is D or R, $X_5$ is N or E, $X_6$ represents the C-terminal part; and wherein one or more of the amino acids of the core sequence may be derivatized. Furthermore, either the N-terminal part of the sequence is acetylated, and/or the C-terminal part is amidated, and/or the amino acid sequence is different from $X_1KEFKRIVQRIKDFLRNLVX_6$ (SEQ ID NO:2). By virtue of the affinity to microbial toxins, the compounds can be therapeutically used to manage conditions associated with the presence of such toxins in the body. By virtue of their direct antimicrobial activity, however, they can also be used as, or in the place of, antibiotics. The dual activity makes these compounds extremely useful both when administered alone and in combination with other antibiotics whose undesired side effects, such as the generation of resistant microorganisms or the toxic effects of microbial toxins which are released into the body when large numbers of germs are killed within the body, may be inhibited or alleviated.

In this description and the appending claims the terms "wherein the N-terminal part is acetylated" have the following meaning. The N-terminal part is protected by reaction with a carboxylic acid to obtain an amide linked stabilizing or protecting group. It is, for instance, possible to react the peptide with fumic acid to obtain a formyl stabilized peptide; with acetic acid to obtain an acetyl protected peptide. Further the peptide can be reacted with propionic acid and other organic acids having up to 6 carbon atoms and even up to 10 carbon atoms in the carbohydrate part R. In these organic acids the carbohydrate group is R having up to 10 carbon atoms, may be straight, or branched, or cyclic and/or may contain one or more unsaturations. Moreover, the alkyl chain can be substituted with e.g. hydroxyl, halogen, amino, mercapto and sulphuroxide groups. Hence, at the N-terminal part the following group can be present: —C(O)—R'. Alternatively, instead of reaction with a carboxylic acid, the reaction can also be carried out with a sulphonic acid to obtain the corresponding sulfonamide linkage. Hence, at the N-terminal part the group —$SO_2$—R may be present. Alternatively, the said terms also encompass alkylation and dialkylation so that at the N-terminal part a secondary or tertiary amine group —N—$(R)_1$ or N—$(R)_2$ may be present wherein each R has the above meaning.

In yet a further embodiment the "acetylation" encompasses reaction of the peptide with an isocyanate or an isothiocyanate in which case a urea or thiourea is created: —R—N—C(O)— or R—N—C(S)— respectively, R being as defined hereinabove.

Finally, the N-terminus can be protected by an acid stable blocking group, which group is conventionally introduced during peptide synthesis, but will now not be removed. Well-known blocking groups are the $F_{moc}$ and Z-group.

As to the meaning of the terms "wherein the C-terminal part is amidated" the following is noted. The term "amidation" means that the —OH naturally present as the C-terminus is replaced by the group —X, wherein X is (i) a —$NY_2$ group, Y, independently being H, or R, wherein R is as defined hereinabove or the two Y-groups together may be a cyclic moiety together with the N-group to which they are attached, preferably at least one R group is present; (ii) an —OR group wherein R is as defined hereinabove, or (iii) a —R group. The peptide amides are preferred because these have the highest stability.

The peptidic compounds of the present invention have been found to have an optimized stability compared to the native amino acid sequence excluded from claim 1.

Peptidic compounds are peptides, such as oligo- or polypeptides, proteins, or substances derived from peptides. Beyond peptides themselves, peptidic compounds also encompass analogues of peptides, peptide derivatives, modified peptides, and peptide conjugates. Peptidic compounds have in common that they comprise amino acid sequences. More precisely, peptides are defined as amides that are derived from two or more amino acids by combination of the amino group of one acid with the carboxyl group of another (Merriam Webster Medical Dictionary 2001). A peptidic compound, in contrast, may also refer to a peptide structure within a molecule. Typically, peptides are composed of naturally occurring (L-)α-amino acids, in particular alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

Analogues or functional equivalents of peptides are peptidic molecules, comprising the same activity and especially the same affinity to microbial and especially to bacterial toxins in kind, but not necessarily in amount, and may, for instance, be modified peptides, peptoids, peptide analogues or peptidomimetics.

Modified peptides are molecules derived from peptides by the introduction of substituents or functional groups which are, generally, not present in naturally occurring amino acids. The term also includes compounds which are obtained by the reaction of peptides with molecules from other chemical categories, whether these molecules are naturally occurring or not. For instance, phosphorylated, sulfonated and biotinylated peptides, glycoproteins, and lipoproteins are frequently found in nature, while peptides modified with polyethylene glycol are examples of chemically modified peptides that have been designed to alter some, but not all of the peptides' properties.

Peptoids, like peptides, are also peptidic compounds. They are also typically amides of two or more amino acids. However, they are frequently not directly derived from naturally occurring amino acids, but rather of various types of chemically synthesized L- and/or D-amino acids.

Peptidomimetics, in their broadest scope, are compounds which are in their functional structure more or less similar to a peptide, but which may also contain non-peptidic bonds in the backbone, or D-amino acids. In general, peptidomimetics serve as substitutes for native peptides in the interaction with receptors and enzymes (Pharmaceutical Biotechnology, Ed. D. J. A. Crommelin and R. D. Sindelar, Harwood Academic Publishers, 1997, p. 138). Pseudopeptides, a class of peptidomimetics, are compounds containing amide bond isosteres instead of amide bonds (ibid., pp. 137-140).

The compounds which are used to carry out the invention also include salts of peptides or functional equivalents, such as pharmaceutically acceptable acid- or base addition salts, and adducts. They also include multimers of peptides or functional equivalents.

Furthermore, the compounds have affinity to at least one toxin, and especially a bacterial toxin. In a large number of infectious diseases, bacterial toxins, such as the class of lipopolysaccharides (LPS) in the case of gram-negative bacteria, and lipoteichoic acid in the case of gram-positive bacteria, are involved in the manifestation of the disease. These toxins can induce substantial inflammatory reactions. For instance, in upper airway infections, the inflammation may lead to mucosal damage of the epithelial of the middle ear or the sinuses, resulting in the impairment of the mucociliary clearance system (MCS), which is one of the major defence systems of the upper airways. Affinity to the fungal or bacterial toxins is a prerequisite of any neutralization capability, and preferably, the compounds of the invention not only bind to LPS and other toxins, but also have the ability to neutralize or inhibit these toxins or otherwise reduce the effects of said toxins.

The desired type of activity against bacteria and fungi, and bacterial and fungal toxins, is observed when peptidic compounds fulfill the structural requirements as defined in claim 1, according to which the compounds comprise an amino acid sequence X₁KEFX₂RIVX₃RIKX₄FLRX₅LVX₆ (SEQ ID NO:1), wherein X₁ represents the N-terminal part of the sequence, X₂ is K or E, X₃ is Q or E, X₄ is D or R, X₅ is N or E, and X₆ represents the C-terminal part. This basic motif is derived from the natural antimicrobial protein CAP18, or the peptide LL-37 which is itself derived from CAP18.

As used herein, the N-terminal part is a group, atom, or sequence representing the N-terminal moiety or domain of the compound, i.e. the structure that is attached to the terminal α-amino group of the core sequence which is not involved in an amide bond within the sequence. The N-terminal part may simply be a hydrogen atom in the case of a free α-amino group; or it may consist of a chemical group attached to the terminal α-amino nitrogen atom, such as an acyl group. It may also represent a larger group, such as a sequence of two or more amino acids, or a chemical structure which is not composed of or not solely composed of amino acids. The C-terminal part is defined in an analogue fashion.

Preferably, the compounds comprise a total of more than the 18 amino acids defining the core motif. In one embodiment, the N-terminal part comprises a sequence of two or more amino acids. Among the amino acids which are suitable members of this sequence are I and G, and a preferred N-terminal part is IG.

In another embodiment, the C-terminal part also comprises an amino acid sequence. The sequence may comprise 1, 2, 3, 4, or more than 4 amino acids. In one embodiment, the C-terminal part comprises 4 amino acids. The C-terminal end of said C-terminal part of 4 amino acids may be an E, as in the equivalent position within peptide LL-37. However, this C-terminal end may also be defined by an R. The amino acid which is positioned next to the C-terminal amino acid may be T as in LL-37, or it may be L. P and R are two other preferred members of the 4 amino acid sequence of the C-terminal part, in either of the two remaining positions. Most preferably, the C-terminal part is selected from the sequences PRTE (SEQ ID NO:5) and RPLR (SEQ ID NO:6).

In a further embodiment, the N-terminal part and the C-terminal part are selected from the preferences described above to yield a peptidic structure with a total number of 24 amino acids. Among the presently most preferred compounds are the peptides IGKEFKRIVQRIKDFLRNLVPRTE (SEQ ID NO:3) and IGKEFKRIVERIKRFLRELVRPLR (SEQ ID NO:4), either as peptides themselves, or as modified or derivatized peptides.

Among the preferred modifications are amidated and/or acetylated peptides. One of the positions in which amidation seems particularly advantageous is the C-terminus of the peptide. Acetylation, on the other hand, is preferably performed at the N-terminal amino acid. In one of the presently preferred embodiments, the peptides IGKEFKRIVQRIKDFLRNLVPRTE (SEQ ID NO:3) and IGKEFKRIVERIKRFLRELVRPLR (SEQ ID NO:4) are both N-terminally acetylated and C-terminally amidated. Preliminary testing suggested that these modifications possess an increased stability in the presence of exo-peptidases.

The compounds can generally be prepared by methods that are known for the preparation of peptides and similar substances. Smaller compounds containing only a few amino acids or similar units, and preferably not more than 30-50 units, can be prepared by chemical or enzymatic ligation techniques, either using the classical approach in which the reactions take place in solution or suspension, or by employing the more modern solid phase approach, in which the peptide is assembled while being anchored to a solid surface, such as a polymeric bead. Larger compounds are typically synthesized by automatic solid phase peptide synthesizers.

Alternatively, the compounds can be prepared by known genetic engineering techniques. This approach is especially valid if the compound is indeed a peptide or a slightly modified peptide. For instance, a DNA sequence which encodes the compound can be associated or combined with an expression vector capable of transfecting cells. In another step of the method, host cells or target cells are transfected with said DNA by contacting the cells with the vector and the vector-associated DNA under conditions which allow transfection. In a further step, the host or target cells are cultured under conditions which allow the expression of the compound. Subsequently, the compound can be isolated. If the compound itself cannot be encoded or expressed but is very similar to a peptide that can be encoded or expressed, the method can be applied to prepare the peptide to which the compound is similar, followed by one or more steps wherein the peptide is modified by chemical or enzymatic techniques to prepare the compound.

Various types of vectors are used for this purpose, such as viral vectors, lipoplexes, polyplexes, microspheres, nanospheres, dendrimers, naked DNA, peptide delivery systems, lipids, especially cationic lipids, or liposomes made thereof, polymeric vectors, especially those made of polycationic polymers. Among the preferred viral vectors are retroviruses, adenoviruses, adeno-associated viruses, herpes simplex viruses, and virosomes. Preferred non-viral vectors include chitosan, SPLP, polymeric systems based on PLGA, polyethylene imines, polylysines, polyphosphoamidates, poly(meth)acrylates, polyphosphazenes, DOPE, DOTAP, and DOTMA.

Some more comprehensive summaries of methods which can be applied in the preparation of the compounds of the invention are described in: W. F. Anderson, Nature 392 Supp., 30 Apr. 1998, p. 25-30; Pharmaceutical Biotechnology, Ed. D. J. A. Crommelin and R. D. Sindelar, Harwood Academic Publishers, 1997, p. 53-70, 167-180, 123-152, 8-20; Protein Synthesis: Methods and Protocols, Ed. R. Martin, Humana Press, 1998, p. 1-442; Solid-Phase Peptide Synthesis, Ed. G. B. Fields, Academic Press, 1997, p. 1-780; Amino Acid and Peptide Synthesis, Oxford University Press, 1997, p. 1-89.

Salts of peptides or functional equivalents are prepared by known methods, which typically involve the mixing of the peptide or peptoid with either a pharmaceutically acceptable acid to form an acid addition salt, or with a pharmaceutically acceptable base to form a base addition salt. Whether an acid or a base is pharmaceutically acceptable can be easily decided by a person skilled in the art after taking the specific intended use of the compound into consideration. For instance, not all acids and bases that are acceptable for in vitro diagnostic compositions can be used for therapeutic compositions. Depending on the intended use, pharmaceutically acceptable acids include organic and inorganic acids such as formic acid, acetic acid, propionic acid, lactic acid, glycolic acid, oxalic acid, pyruvic acid, succinic acid, maleic acid, malonic acid, cinnamic acid, sulphuric acid, hydrochloric acid, hydrobromic acid, nitric acid, perchloric acid, phosphoric acid, and thiocyanic acid, which form ammonium salts with free amino groups of peptides and functional equivalents. Pharmaceutically acceptable bases, which form carboxylate salts with free carboxylic groups of peptides and functional equivalents, include ethylamine, methylamine, dimethylamine, triethylamine, isopropylamine, diisopropylamine, and other mono-, di- and trialkylamines, as well as arylamines. Moreover, also pharmaceutically acceptable solvates, complexes or adducts, such as hydrates or ethurates are encompassed.

Some of the preferred modifications of the peptides may be easily introduced during or at the end of the synthesis. For instance, when the peptide is synthesized using a solid-phase technique, N-terminal acetylation can be performed at the end by reacting the amino acid sequence, which is still bound to the resin, with acetic acid instead of with another amino acid.

C-terminal amidation, on the other hand, can be performed by using a special kind of resin in solid-phase peptide synthesis, such as the commercially available Tentagel S AM (ex Rapp, Tübingen, Germany). These resins comprise a chemical "handle" from which amidated peptides are released during the cleavage. These and further methods of modifying peptides are known to any person skilled in the art.

As previously mentioned, the compounds have an affinity to microbial toxins and especially to bacterial toxins, such as lipopolysaccharide (LPS) and lipoteichoic acid (LTA). Therefore, the compounds can be used advantageously for preventive, therapeutic and diagnostic purposes in conditions and diseases in which the presence of these toxins is involved. The binding ability will typically lead to neutralization of the toxins, by virtue of which the compounds may be considered antagonists or partial antagonists. Furthermore, they may be used as targeting agents or ligands for other compounds which are capable of neutralizing the toxins, and which may be specifically targeted to these toxins through covalent or non-covalent ligation with the compounds, or through being covalently or non-covalently bonded to the surface of a drug carrier such as a liposome, a nano- or microparticle, a nano- or microcapsule, a lipid complex, or a micelle.

In diagnosis, the compounds may be used for the detection of, or the quantification of the amount of, bacterial toxins present in physiological fluids, such as the blood, plasma, serum, the mucus lining a mucosal epithelium, such as of the respiratory tract, or in fluids whose presence results from a pathological condition, such as the fluid found in the middle ear in otitis media with effusion (OME). For this use, the compounds may be incorporated into diagnostic kits to be used in vitro, or into diagnostic compositions which may be administered to a patient. For this use, an option is to conjugate a compound of the invention with a chelator, which is subsequently complexed with an isotopic label that is detectable by an appropriate monitoring system.

In a preferred use, the compounds are administered as active drug substances to prevent or treat diseases and conditions related to fungal and bacterial infections and the presence of fungal and bacterial toxins in the body. As mentioned before, there are certain disadvantages and limitations of conventional antibiotics in the therapy of acute or chronic infections, such as the induction of tolerance and the selection of tolerant bacterial variants, the depression of the patient's natural defence systems, the impairment of the bacterial flora naturally populating the mucosae, the release of large amounts of bacterial toxins as the germs are killed etc. Furthermore, there may be conditions and diseases in which the presence of toxins and especially bacterial toxins, and not the presence of the micro-organisms per se, is the major cause, such as in OME, wherein the local retention of toxins in the middle ear may significantly contribute to the manifestation of the disease even in the absence of symptoms of an acute infection.

However, since the compounds also have pronounced antimicrobial activity, they can be used even in those conditions in which it is essential to actually reduce the number of microorganisms infecting the body, such as severe acute infections. In this respect, they can replace or complement other antibiotics, even in diseases and conditions which could not be treated with compounds capable of neutralising microbial toxins alone. Examples of such diseases are acute bacterial or fungal infections, such as septic shock, acute infections of the eye(s), liver, kidney(s), lungs, bronchi, nasal or frontal sinus, ear(s), vagina, urethra, skin, central nervous system, cardiac muscle, spleen, or other tissues and organs. An example of a particularly severe condition associated with an infection is septic shock.

In all these cases, it may be advisable to treat the disease not with antibiotic drugs, but with substances which are capable of neutralizing the bacterial toxins. For this aim, the compounds of the invention are particularly advantageous because they show a high binding and neutralization activity against the most relevant microbial toxins, such as lipopolysaccharide (LPS) in the case of gram-negative bacteria, and lipoteichoic acid (LTA) in the case of gram-positive bacteria. In infections of the upper airways, for the treatment of which the compounds of the invention are particularly preferred, these bacterial products can induce an inflammation reaction in the middle ear or in the sinuses, and can induce mucosal damage of the upper airway epithelia. Neutralizing the toxins involved may allow the mucosal damage including the impairment of the mucociliary clearance system (MCS) to be prevented, controlled, or reduced, and will thus strengthen the natural defence systems. In those cases including OME, in which bacterial toxins may represent the major problem even in the absence of significant numbers of living bacterial cells, a therapy relying on the administration of a compound of the invention, for instance directly to the middle ear, may represent the primary therapeutic approach. But also in other airway infections, such as acute or chronic sinusitis, or acute or chronic otitis, the compounds may be highly useful for the restoration of the normal mucosal functions and their natural defence systems.

More generally speaking, the compounds of the invention are useful agents in the prevention and therapy of conditions consisting in, and arising from, infective bacteria including *Streptococcus pneumoiae*, *Haemophilus influenzae*, *Moraxella catarrhalis*, group A β-hemolytic streptococci, *Staphylococcus aureus*, gram-negative enteric bacilli, *Streptococcus pyrogenes*, *Escherichia coli*, gram-negative bacilli, *Pseudomonas* sp.

The infections which are prevented or managed with the compounds of the invention may be caused by microorganisms which are in essence planktonic, that is, their habitus is that of individual microbial organisms. If planktonic microorganisms, for example, have infected a physiological fluid of a mammal such as blood, they may be transported with the bloodstream throughout the body of the mammal.

Systemic or generalised infections which may at least in part be caused by planktonic microorganisms include acute or chronic fungal infections such as actinomycosis, blastomycosis, nocardiosis, cryptococcosis, sporotrichosis, sporotrichosis, coccidiomycosis, and aspergillosis, as well as acute or chronic bacterial infections such as anthrax, tetanus, gangrene, botulism, listeriosis, typhus, Legionnaire's disease, cholera, yellow fever and the like. Acute serious systemic infections may be associated with septic shock, which is a life-threatening severe form of sepsis that usually results from the presence of large numbers of gram-negative bacteria and their toxins in the bloodstream, and which is further characterised by decreased blood flow to organs and tissues, hypotension, organ dysfunction, impaired mental state, and often multiple organ failure, and which often affects immunocompromised individuals.

In more recent years, however, it has been found that many infectious diseases and conditions are also, at least in part, caused by microorganisms which form more sessile communities, usually referred to as biofilms. This is true both for many systemic and—in particular—for a large number of more localised infections. As used herein, a biofilm is a microbially derived sessile community characterised by cells that are attached to a substratum or interface or to each other, are embedded in a matrix of extracellular polymeric substances that they have produced, and exhibit an altered phenotype with respect to growth rate and gene transcription. Usually, the extracellular matrix comprises a highly hydrated, predominantly anionic matrix polymer. Biofilms can adhere to surfaces and interfaces; in fact, adhesion may trigger the expression of genes controlling the production of the extracellular matrix and the conversion of the previously planktonic microorganisms into their sessile phenotypes.

It is believed that sessile microorganisms and their biofilms play a major role in a number of infectious diseases, and for some of them this has been supported by a large body of evidence. Among these diseases are e.g. periodontitis, native valve endocarditis, cystic fibrosis, chronic bacterial prostatitis, bronchitis, pneumonia, sinusitis, dental caries, chronic tonsilitis, endocarditis, necrotising fascitis, musculoceleteral infections, osteomyelitis, biliary tract infections, infectious kidney stones, and otitis media. Most likely, many other—in particular local—infections involving particular regions or organs of the body also involve sessile microorganisms, such as infections of the liver, the spleen, the periodontium, an eye, a kidney, the skin, the vagina, the urethra, or the heart.

In the investigation of the activity of the peptidic compounds as defined in claim 1, it has now been found that these compounds are also active against sessile, biofilm-forming microorganisms. Thus they represent useful compounds for the prevention or therapy of diseases related to such microorganisms, or involving the sessile state of microorganisms. For example, it has been found that certain microorganisms capable of forming biofilms on certain surfaces such as PVC, e.g. *Pseudomonas putida*, could be inhibited and prevented from forming biofilms in a standard biofilm assay.

The inhibition effect may be achieved when a compound of the invention is present at a concentration of at least about 0.001 µM, and more preferably of at least about 0.01 µM, and still more preferably at least about 0.1 µM. In a further preferred embodiment, the concentration of the compound is about 0.1 to about 100 µM. However, depending on the type and amount of fluid which contacts the biofilms, and the specific microorganism involved, these concentrations may be adapted.

Furthermore, it has been found that the compounds of the invention not only prevent the formation of biofilms by microorganisms otherwise capable of microfilm formation, but are also active against microfilms that have formed already. Depending on their concentration, they are capable of disrupting or degrading biofilms, as detectable e.g. in standard biofilm assays. Again, the concentration of the compound should be selected by taking into account the type and amount of fluid which contacts the biofilms and the specific microorganism involved. For example, it has been found that concentrations as low as about 0.001 µM may already have a disruptive effect on pre-formed biofilms. Thus, it is preferred that the concentration of the compound is selected to be at least about 0.001 µM. Other preferred concentrations are at least about 0.01 µM, 0.1 µM, 0.1 µM, 10 µM and 100 µM, respectively.

A particular risk from biofilm infections arises from the insertion or implantation of medical devices in the body of a human, or other mammal, whether for diagnostic or therapeutic purposes. For example, the involvement of biofilms has been demonstrated for infections from contact lenses, heart valves, venous catheters, urinary catheters, intrauterine devices, sutures, vascular grafts and shunts, peritoneal dialysis devices, penile prostheses, and orthopedic prostheses. Thus, it is another preferred embodiment to use the compounds of the invention to prevent or manage an infection resulting from such devices.

A particular advantage of the compounds of the invention over the native proteins and peptides from which they are derived, such as CAP18 and LL-37, is their low degree of undesirable inflammatory activity. This activity is related to the various cellular processes, including proliferation, differentiation and expression of genes encoding pro-inflammatory mediators like cytokines. Cytokines are direct mediators of inflammation and influence the progress and direction of many immunological reactions. Perturbation of the balance in cytokine production is widely recognized as a critical factor in several disease states. In a condition such as otitis media with effusion or sinusitis, this balance is already disturbed. T cell proliferation is also not favourable in this situation, because this will further stimulate the immune response that is already out of control.

Thus, the compounds can be advantageously used in pharmaceutical compositions. According to the invention, such pharmaceutical compositions are provided as well as the compounds themselves. As used herein, the term "pharmaceutical composition" refers to therapeutic and diagnostic compositions, as well as to medicaments and diagnostics containing such compositions. Therapeutic compositions and medicaments are used for the prevention or treatment of diseases and other conditions of mammals whose improvement is desirable. Diagnostics and diagnostic compositions are used for the diagnosis of such diseases in vivo and in vitro.

Typically, such a medicament, or composition, comprises at least one compound of the invention as active ingredient and at least one pharmaceutically acceptable carrier or excipient.

In one of the embodiments, the medicament comprises another active ingredient, which may be selected from the same group of compounds as specified in claim 1. Alternatively, the other compound belongs to a different group. For example, it may be a compound also known to have antibiotic or antifungal activity, but with a different mechanism of action. In a further embodiment, the other compound is not incorporated into the same medicament, but co-administered as a separate formulation.

Furthermore, the composition is processed and shaped in such a way that it can be administered to a human being, or to an animal. As used herein, a carrier or excipient is any pharmaceutically acceptable substance or mixture of substances having no substantial pharmacological activity, which can be used as a vehicle or as an auxiliary substance to formulate a compound into dosage form which is stable and suitable to administer. Examples of pharmaceutically acceptable excipients are known to the skilled man and can be found in the monographs of the major pharmacopoeias.

In one embodiment, the composition is formulated and processed for parenteral injection, instillation or irrigation, preferably for intravascular injection, such as intravenous or intra-arterial, but also for intramuscular, subcutaneous, intralesional, intraperitoneal, locoregional or other routes of parenteral administration. In another preferred embodiment, the composition is administered directly to the affected mucosa of the upper airway, such as the middle ear. The same principles that govern the formulation of other drugs for these administration routes will also teach those skilled in the arts how to prepare such compositions. For instance, one of the requirements of parenteral dosage forms is their sterility. Other requirements are described in all major pharmacopoeias, such as in USP 24, in the monograph "General Requirements for Tests and Assays. 1. Injections", p. 1775-1777. To increase the stability of a parenteral formulation, it may be necessary to provide a dried dosage form which must be reconstituted before it can be administered. An example of such a dosage form is a freeze-dried or lyophilized formulation. Suitably, the compositions of the invention may also contain a mucolytic solvent.

It may be desirable to administer a compound of the invention as a parenteral controlled release dosage form to avoid frequent injections and to improve the effectiveness and convenience of the therapy. Various methods of preparing such depot formulations are known. Prolonged release may be provided by solid implants, nanoparticles, nanocapsules, microparticles, microcapsules, emulsions, suspensions, oily solutions, liposomes, or similar structures.

In the case of compositions which are to be administered locally to an affected mucosa, it may be useful to provide a formulation having properties which provide for an extended time of local retention at the site of administration to increase the effectiveness of the medication. To achieve this goal, mucoadhesive excipients may be incorporated into the formulation. Such functional excipients are known to the person skilled in the art; they include polymers such as polyacrylic acids and derivatives thereof, polymethacrylic acids and their derivatives, cellulose ethers including hydroxypropyl methylcellclose, carboxymethylcellulose, starches, chitosan etc. Suitably or alternatively, the compositions of the invention may also contain a mucolytic solvent. Particularly, mucolytic solvents are used to affect the permeability of the peptidic compound of the invention into the mucus, e.g. in the respiratory tract. Suitable solvents may comprise known muco-regulatory or mucolytic agents such as N-acetylcysteine, S-carboxymethyl cysteine, bromhexine, ambroxyl, DNAse, erdosteïne, saline solution and nesosteine. Preferably, bromhexine is used.

Further excipients that are particularly useful for the preparation of parenteral formulations in their broadest definition are solvents, cosolvents and liquid or semisolid carriers, such as sterile water, ethanol, glycerol, propylene glycol, polyethylene glycol, butanediol, fatty oils, short- and medium chain triglycerides, lecithin, polyoxyethylene castor oil derivatives; substances to adjust the osmolality and pH, such as sugars, especially glucose, sugar alcohols, especially mannitol, sodium chloride, sodium carbonate, citric acid, acetate, phosphate, phosphoric acid, hydrochloric acid, sodium hydroxide etc.; stabilizers, antioxidants, and preservatives, such as ascorbic acid, sodium sulphite or -hydrogen sulphite, EDTA, benzyl alcohol etc.; other excipients and lyophilization aids, such as albumin, dextran etc.

Similarly, it may be advantageous to administer a compound of the invention in a transmucosal dosage form. This route of administration is non-invasive and patient-friendly; at the same time it generally leads to an improved bioavailability of the compound of the invention as compared to oral administration, especially if the compound is not stable in the fluids of the digestive system, or if it is too large to be absorbed from the gut effectively. Transmucosal administration is possible, for instance, via nasal, buccal, sublingual, gingival, or vaginal dosage forms. These dosage forms can be prepared by known techniques; they can be formulated to represent nasal drops or sprays, inserts, films, patches, gels, ointments, or tablets. Preferably, the excipients used for a transmucosal dosage form also include one or more substances providing for mucoadhesion, thus prolonging the contact time of the dosage form with the site of absorption and thereby potentially increasing the extent of absorption.

Alternatively, the pharmaceutical compositions may be designed for oral administration and processed accordingly. Appropriate oral dosage forms include tablets, hard capsules, soft capsules, powders, granules, orally disintegrating dosage forms, syrups, drops, suspensions, effervescent tablets, chewable tablets, oral films, lyophilized dosage forms, sustained release dosage forms, controlled release dosage forms. In one of the preferred embodiments, the oral dosage form is an enterically coated solid dosage form to provide protection of the compound from the acidic and proteolytic environment of the stomach.

In a further embodiment, the compounds are administered via the pulmonary route, using a metered dose inhaler, a nebulizer, an aerosol spray, or a dry powder inhaler. Appropriate formulations can be prepared by known methods and techniques. Transdermal, rectal, or ocular administration may also be feasible in some cases.

It can be advantageous to use advanced drug delivery or targeting methods to deliver a compound of the invention more effectively. For instance, if a non-parenteral route of administration is chosen, an appropriate dosage form may contain a bioavailability enhancing agent, which may be any substance or mixture of substances which increases the availability of the compound. This may be achieved, for instance, by the protection of the compound from degradation, such as by an enzyme inhibitor or an antioxidant. More preferably, the enhancing agent increases the bioavailability of the compound by increasing the permeability of the absorption barrier, which is typically a mucosa. Permeation enhancers can act via various mechanisms; some increase the fluidity of mucosal membranes, while others open or widen the gap junctions between mucosal cells. Still others reduce the viscosity of the mucus covering the mucosal cell layer. Among the preferred bioavailability enhancers are amphiphilic substances such as cholic acid derivatives, phospholipids, ethanol, fatty acids, oleic acid, fatty acid derivatives, EDTA, carbomers, polycarbophil, and chitosan.

Making use of the antimicrobial and antifungal activity of the compounds, it is an option to use them for the manufacture of medicaments which either contain no preservatives or only at a reduced content. By "reduced content" is meant that the preservative content is lower than the preservative content needed to effectively preserve the corresponding placebo composition, which is a composition which contains the same components except for the active ingredient.

Whether a composition is effectively preserved can be determined with appropriate tests, such as the test for preservative efficacy (e.g. USP <51>), wherein five challenge organisms are tested at defined time intervals, depending on the product category. Conducted in appropriate series, such testing can also be performed in order to determine the minimally effective concentration of a specific preservative for a given composition, such as a drug-free composition corresponding to a composition as described above.

For example, it may be found that in order to effectively preserve a particular placebo composition with sorbic acid, the preservative must be present at a concentration of at least about 0.1% (w/v). In this case, the reference composition which comprises the compound specified in claim 1 could contain sorbic acid at a substantially lower concentration, such as about 0.05% (w/v) or less. In another embodiment, the concentration of the preservative is selected to be not more than about a fifth, and more preferably not more than about a tenth, of the concentration needed to effectively preserve a corresponding placebo composition.

The following examples are intended to further illustrate the invention, not to limit its scope to the embodiments presented herein.

EXAMPLE 1

Preparation of Compounds

The following peptidic compounds, each of them comprising 24 amino acids, the compounds herein coded as P60, P60.4, P60.Ac, and P60.4Ac were prepared by solid phase strategies on an automated multiple peptide synthesizer (SyroII, MultiSyntech, Witten, Germany). For P60 and P60.4, Tentagel S AC (Rapp, Tübingen, Germany), a graft polymer of polyethylene glycol and polystyrene was used as a resin (loading 0.2 meq, particle size 90 μm). For P60.Ac and P60.4Ac, Tentagel S AM was used, which yields a C-terminally amidated peptide. Repetitive couplings were performed by adding a six fold molar excess (based on the resin loading) of a 0.60 M solution of the appropriate Fmoc amino acid in NMP, a six fold molar excess of 0.67 M PyBOP in NMP and a twelve fold molar excess of NMM in NMP 2/1 (v/v) to the reaction vessel. Side chain protection was as follows: tBu for D, E, S, T; Boc for K; Trt for N, Q and Pmc for R. Fmoc-deprotection was performed by adding 3 times piperidine/NMP 1/4 (v/v) to each reaction vessel. Coupling- and deprotection times were 45 min and 3 times 3 min. respectively. Washings after couplings and Fmoc-deprotections were performed 6 times with NMP. For P60.Ac and P60.4Ac, N-terminal acetylation was performed with acetic acid while the peptide was still bound to the resin. After synthesis the peptidyl resins were washed extensively with NMP, dichloromethane, dichloromethane ether 1/1 (v/v) and ether respectively, and air dried. Peptidyl resins were then cleaved and side chain deprotected in TFA/water 95/5 (v/v) for 2.5 h (1.5 ml per 10 μmol of peptide), the resin was removed by filtration and the peptide was precipitated from the TFA solution with ether/pentane 1/1 (v/v) (10 ml per 10 μmol of peptide). The solution was cooled for 1 h at –20° C. and the precipitated peptide was isolated by centrifugation (–20° C.; 2,500 g, 10 min.). After triturating and vortexing of the pellet with 10 ml ether/pentane 1/1 (v/v) and isolation by the same procedure, the peptides were air dried at room temperature for 1 h. Peptides were dissolved in 2 ml water or 2 ml 10 vol % acetic acid, the solution was frozen in liquid nitrogen for about 5 min and subsequently lyophilized while being centrifuged (1,300 rpm, 8-16 h). The analysis of the peptides was performed with RP-HPLC and Maldi-T of mass spectrometry.

The amino acid sequences of the compounds are:

```
P60         IGKEFKIRVQRIKDFLRNLVPRTE
            (SEQ ID NOT: 3)

P60.Ac*     IGKEFKRIVQRIKDFLRNLVPRTE
            (SEQ ID NOT: 3)

P60.4       IGKEFKRIVERIKRFLRELVRPLR
            (SEQ ID NOT: 4)

P60.4Ac*    IGKEFKRIVERIKRFLRELVRPLR
            (SEQ ID NOT: 4)
*The suffix Ac means that the peptide is
N-terminally acetylated and C-terminaliy
amidated.
```

EXAMPLE 2

Neutralization of Toxins

The compounds prepared according to example 1 were tested for their capability to neutralize the bacterial toxin LPS with a limulus amoebocyte lysate (LAL) assay and with a whole blood (WB) assay. LTA neutralization was also measured with a whole blood assay. Peptide LL-37 was used as a positive control. The peptide concentration whereby 50% LPS is neutralized was used as a measure of the peptide's activity. These concentration values were as in table 1. The differences between the compounds within each assay were not statistically significant. In summary, the tested compounds of the invention showed approximately the same degree of anti-toxin activity as the native antimicrobial peptide LL-37.

TABLE 1

Compound concentrations for 50% LPS- and LTA-neutralization (in μg/ml ± SD)

| Compound | LPS (LAL) | LPS (WB) | LTA (WB) |
| --- | --- | --- | --- |
| P60 | 1.5 ± 0.5 | 1.4 ± 0.1 | 2.1 ± 0.7 |
| P60.Ac | 1.8 ± 0.8 | 2.4 ± 0.5 | 2.1 ± 0.1 |
| P60.4 | 1.7 ± 0.6 | 2.1 ± 0.6 | 2.0 ± 1.3 |
| P60.4Ac | 1.8 ± 0.1 | nd | Nd |
| LL-37 (control) | 1.3 ± 0.2 | 1.2 ± 0.2 | 1.6 ± 0.5 |

EXAMPLE 3

Immunologic Cell Activation by Compounds

The compounds prepared according to example 1 were tested for their therapeutically undesirable immunogenic activity by using Elispot, T-cell proliferation, ERK-activation, and neutrophil chemotaxis assays. The Elispot assay is applicable to determine effects of drugs, chemicals or other compounds on cytokine secretion in vitro, thereby providing data on their putative modulatory effects on immune function in vivo. The results of the assay are given as fraction of positive responses to IFN-gamma. ERK-(extracellular signal-related kinases)-1/2 is part of the MAP-kinase signaling pathway, that has been shown to be involved in various cellular processes, including proliferation, differentiation and expression of genes encoding pro-inflammatory mediators like cytokines. Cytokines are direct mediators of inflammation and influence the progress and direction of many immunological reactions. Perturbation of the balance in cytokine production is widely recognized as a critical factor in several disease states. This balance is already disturbed in the case of conditions such as otitis media with effusion and sinusitis. T cell proliferation is also not favorable in this situation, because this will also stimulate the immune response that is already out of control. It is therefore desirable that the compounds of the invention do not stimulate cytokine production, T cell proliferation, ERK-activation or chemotaxis of neutrophils.

For T cell proliferation, 150,000 peripheral blood mononuclear cells (PBMC) were cultured in the absence or presence of 10 g/ml of the compounds for 5 days in 96 well round bottom plates (Costar Inc. Cambridge, Mass.) in a final volume of 150 μl IMDM complete. As a positive control, PBMC were cultured in the presence of 25 U/ml recombinant IL-2. During the final 20 hours of culture, PBMC were pulsed with [3H]thymidine (0.5 microCi/well), after which 3H-incorporation was measured by liquid scintillation counting. For detection of the T cell cytokines IFN and IL-10 by E is pot analysis, 1.5×10$^6$ PBMC were cultured in 0.5 ml IMDM complete in the absence or presence of various concentrations of synthetic peptide. As a positive control PBMC were stimulated by 10 μg/ml poke weed mitogen (PWM). After 48 hours of culture, PBMC were harvested by gently rinsing the wells with warm IMDM to collect non-adherent cells, which were washed in a large volume of IMDM. PBMC were subsequently plated on antibody-precoated ELISA plates and cultured for 5 hours in IMDM supplemented with 2% pooled human AB serum at 37° C. 5% $CO_2$, after which the plates were developed according to the manufacturer's protocol (U-CyTech, Utrecht, The Netherlands). Spots were counted on an Olympus microscope and analyzed with Olympus Micro Image 4.0 software (Paes Nederland, Zoeterwoude, The Netherlands). The final results are expressed as fraction of positive stimulation indices (positive: >2).

ERK-1/2 activation was tested with cells from the mucoepidermoid lung tumor cell line NCI-H292 (ATCC, Rockville, Md.), which were cultured in 24- or 6-well tissue culture plates in RPMI1640 medium (Gibco, Grand Island, N.Y.) supplemented with 2 mM L-glutamine (Bio Wittaker, Walkersville, Md.), 200 U/ml penicillin (Bio Wittaker), 200 µg/ml streptomycin (Bio Wittaker) and 10% (v/v) heat-inactivated fetal calf serum (Gibco). After reaching near-confluence, cells were cultured overnight in serum-free medium. Cells were subsequently stimulated for 15 minutes with indicated stimuli. Cellular lysates were prepared using lysisbuffer (0.5% [v/v] Triton X-100, 0.1M Tris-HCl pH 7.4, 100 mM NaCl, 1 mM $MgCl_2$, 1 mM $Na_3VO_4$, mini complete protease inhibitor cocktail [Boeringer Mannheim, Roche, Basel, Switzerland]). Samples were subjected to SDS-PAGE on a 10% glycine-based gel, and resolved proteins were transferred to a polyvinylidene difluoride (PVDF) membrane. Non-specific binding sites were blocked by PBS/0.05% Tween-20/1% casein. The blots were incubated with rabbit polyclonal antibodies against phosphorylated ERK-1/2 (New England Biolabs, Beverly, Mass.), and secondary horseradish peroxidase conjugated anti-rabbit IgG antibodies. The enhanced chemoluminescent (ECL) Western blotting detection system (Amersham Pharmacia Biotech, Upsala, Sweden) was used to reveal immunoreactivity.

Neutrophils chemotaxis was measured with neutrophils isolated from peripheral blood using Percoll density centrifugation (density: 1.082 g/ml). The cells were resuspended at a concentration of 2.5×106 cells/ml in chemotaxis medium (20 mM N-2-hydroxyethylpiperazine-N'-2-ethanesulfonic acid (HEPES buffer) HEPES, 132 mM NaCl, 6 mM KCl, 1.2 mM $KH_2PO_4$, 1 mM $MgSO_4$, 5.5 mM glucose, 0.1 mM $CaCl_2$ and 0.5% (wt/vol human serum albumin [Central Laboratory of the Netherlands Red Cross Blood Transfusion Service (CLB), Amsterdam, The Netherlands] diluted 1:1 with serum-free RPMI. The chemotactic activity of the compounds was assessed using a modified Boyden Camber technique. Briefly, 26 µl stimuli diluted in HEPES buffer was added to the wells of the lower compartment, and 50 µl of neutrophil suspension (2.5×10⁶ cells ml) was added to the upper compartment. The compartments were separated by two filters: a lower filter with a pore size of 0.45 µm (Millipore Products, Bedford, Mass.) and an upper filter with a pore size of 8 µm (Sartorius Filter, San Francisco, Calif.). After incubation for 90 minutes at 37° C., the upper filters were removed, fixed in ethanol-butanol (80:20, vol/vol), and stained with Weigert solution. To determine neutrophil chemotactic activity, neutrophils were counted in six random high-power fields (×400), and the percentage neutrophils on the membrane as compared to the positive control ($10^{-8}$ M N-formylmethionyl-leucyl-phenylalanine (FMLP, Sigma) was calculated.

The results are given in table 2. In summary, the tested compounds of the invention, and in particular P60.4, induced a very low immune response, lower than the natural peptide LL-37. They showed a low ERK-activation and virtually no neutrophil chemotaxis.

TABLE 2

Immunogenicity of compounds

| Compound | γ-IFN Elispot | T cell proliferation | ERK-activation | Chemotaxis (%) |
|---|---|---|---|---|
| P60 | 1/8 | 7/8 | – | 76 ± 39 |
| P60.Ac | 3/8 | 4/8 | ± | 61 ± 36 |
| P60.4 | 3/8 | 2/8 | ± | 0 ± 0 |
| P60.4Ac | nd | nd | ± | 0 ± 0 |
| LL-37 (control) | 4/8 | 6/8 | + | 84 ± 17 |

EXAMPLE 4

In-vivo Tolerability

Compound P60.4Ac was prepared according to example 1 and tested for its tolerability in vivo. More specifically, its potential for causing skin and eye irritation was evaluated in rabbits, whereas its ototoxicity was studied in a guinea pig model. Furthermore, its systemic toxicity was assessed after intravenous administration.

For the skin and eye irritation tests, three rabbits were exposed to 0.5 ml phosphate buffered peptide solution (2 mg/ml), applied onto clipped skin for 4 hours using a semi-occlusive dressing. Observations were made 1, 24, 48, and 72 hours after exposure. Single samples of 0.1 ml of phosphate buffered (pH7.5) peptide solution (2 mg/ml) were instilled into one eye of each of three rabbits to perform an acute eye irritation/corrosion study. Observations were made 1, 24, 48, and 72 hours after instillation.

In result, no skin irritation was detectable. Ophthalmic instillation of the peptide solution resulted in redness of the conjunctivae which resolved completely within 24 hours after instillation.

The systemic toxicity of P60.4c was assessed in a single and repeated dose toxicity study in rats. The peptide was administered daily intravenously in escalating doses. In this phase, the Maximum Tolerated Dose (MTD) was established. Repeated dose toxicity was also studied in the MTD phase. In the dose escalation phase, 9 rats were divided in three groups and received 0.4, 2 or 8 mg/kg/day for two days. Clinical signs were recorded twice daily on days of dosing and one day after dosing, body weights were recorded prior to the first dose and one day after dosing. In the MTD phase, 5 female and 5 male rats received 8 mg/kg/day for 5 following days. Clinical signs were recorded twice daily on days of dosing, body weight on day 1 and 6. Clinical laboratory investigations were performed prior to necropsy. Macroscopy was performed at termination of the MTD phase.

In result, no mortality occurred in the systemic dose escalation study. Furthermore, no clear deviations were noted in clinical signs and body weight. During the MTD phase also no mortality occurred and no clear peptide related findings were noted in clinical signs, body weight, hematology and clinical biochemistry parameters and at macroscopic examination.

EXAMPLE 5

Ototoxicity

To evaluate the ototoxicity of peptide P60.4-Ac, this peptide was tested in guinea pigs (HsdPoc:DH; Harlan, Horst, The Netherlands). Seven healthy male albino guinea pigs (500-1200 g), free of external ear pathology, were used in this study. Animals were anesthetized with intraperitoneal injections of 40 mg/kg ketamine (Eurovet Animal Health B. V., Bladel, The Netherlands) and 10 mg/kg rompun (Bayer A.G., Leverkusen, Germany). After control auditory testing was performed, the auditory bullae were surgically opened to apply a small piece of spongostan to the round window membrane (RWM) and various solutions (approximately 10 µl) were added on the spongostan. The skin was sutured closed and follow-up auditory testing was performed. Application on the RWM was performed in the right ears, the left ears remained untreated. One animal received PBS as a first placebo solution (placebo I), and another animal received the second placebo solution (placebo II), which was 7% Macrogol 10 000 in isotonic [NACl] and preserved [0.02% benzalkonium chloride and 0.1% Na$_2$EDTA] 20 mM phosphate buffer solution (pH 5.5). Two guinea pigs received cisplatin (0.66 mg/ml in PBS, obtained from Sigma Chemicals Zwijndrecht, The Netherlands), which served as a positive control for the test [39]. Peptide P60.4-Ac (2 mg/ml) was tested in PBS solution (formulation I) in one animal and in a buffer corresponding to the second placebo (formulation II) in two other animals.

Auditory brainstem response (ABR) was performed prior to drug administration and directly after surgery and 3, 7, 14 and 22 days later, using a computer-based signal averaging system (Tucker-Davis Technology, Alucha, Fla., USA). Guinea pigs were anesthetized and an insert earphone was placed into the external ear canal. Subcutaneous electrodes were placed over the vertex (active) and over the ipsilateral bulla (reference). Ground electrodes were placed over the neck muscles. ABRs were recorded in an electrically shielded, double-walled, radio-frequency-shielded sound chamber in response to 10 ms tone bursts at 1 kHz. Stimulus intensities were measured and expressed as dB. ABR threshold was defined as the lowest intensity capable of eliciting a replicable, visually detectable response. The post-treatment ABR thresholds were compared to pre-treatment ABR thresholds.

In result, round window application of PBS, which was used as a Control, did not result in a threshold change at 22 days after surgery. Formulation buffer resulted in a threshold change of 2 dB after 22 days. Cisplatin, on the other hand, induced threshold changes of respectively −49 dB and −64 dB, which indicate a severe hearing loss (Table 3). This part of the experiments served as a positive control for the ototoxicity study. Peptide P60.4-Ac (2 mg/1 ml) in PBS induced a threshold change of −7 dB 22 days after surgery. Both animals that received P60.4-Ac as formulation II produced a threshold change of 1 dB.

TABLE 3

Results of ototoxicity evaluation of P60.4Ac

| Group 1 | Placebo I[a] | Cisplatin | | P60.4-Ac Formulation I[a] | Placebo II[b] | P60.4-Ac Formulation II[b] | |
|---|---|---|---|---|---|---|---|
| post-surgery | 1 | −2 | −1 | −2 | 1 | 14 | 20 |
| 3 days | −3 | −32 | −38 | −2 | −8 | −1 | 1 |
| 7 days | −3 | −32 | −45 | 0 | −33[c] | −18 | 2 |
| 14 days | 0 | −30 | −59 | −12 | −1 | 0 | 2 |
| 22 days | 0 | −49 | −64 | −7 | 2 | 1 | 1 |

Values represent Δ presurgery in dB.
[a]PBS
[b]7% Macrogol 10.000 in isotonic [NaCl] and preserved [0.02% benzalkonium chloride and 0.1% Na$_2$EDTA] 20 mM phosphate buffer solution (pH5.5)
[c]Unreliable measurements due to bad wire

EXAMPLE 6

Antimicrobial Activity

Compound P60.4Ac was prepared according to example 1 and sterilised by sterile filtration into 10 mL glass bottles with screw closures. No preservative was added. Separately, a corresponding placebo solution, i.e. a solution with the same components except for compound P60.Ac, was prepared. Samples were drawn from each of the two preparations for conducting a test for antimicrobial activity. In result, the solution containing compound P60.4Ac was found to inhibit bacterial growth or even reduce the number of germs, whereas the corresponding placebo solution showed no antimicrobial activity.

EXAMPLE 7

Antimicrobial Activity

The in vitro antibacterial and antifungal activity of P60.4-Ac and LL-37 were determined as the minimum inhibitory concentrations (MIC) by a microdilution susceptibility test in 96-well microtiter plates, according to a modified version of R. Hancock's "Modified MIC method for cationic antimicrobial peptides" [13]. The antibacterial activity was tested on the reference strains *Escherichia coli* ATCC 8739, *Pseudomonas aeruginosa* ATCC 9027. The antifungal activity was evaluated on *Candida albicans* ATCC 10231 and *Aspergillus niger* ATCC 14406. The antimicrobial activity assay was conducted with different concentrations of P60.4Ac and LL-37 to compare their effects on the bacterial or fungal growth. Antibacterial activity was examined using log-phase cultured bacteria in Trypticase Soy Broth at 37° C. The cultures were diluted with 10 mM Sodium Phosphate buffer pH 7.4 to give approximately $5.0 \times 10^6$ CFU/ml. 10 µl of the diluted test strain was transferred to a 96-well plate and 100 µl of the different peptide concentrations was added to each well. The plates were incubated at 37° C. for 24 hours and are then scored for growth by visual inspection on a light box. They are then returned for incubation for a further 24 hours after which time they are re-evaluated for growth. The yeast strain *C. albicans* was prepared as described above. The filamentous fungi *A. niger* was used as a spore suspension, cultured on Sabourauds Dextrose Agar plates at 20-25° C. for 6-10 days or until adequate sporulation has occurred. The spores were harvested by scrapping and if necessary the concentration was adjusted to a final concentration of $5 \times 10^6$ CFU/ml.

Thus, the antimicrobial activity of P60.4-Ac was evaluated against two Gram-negative strains and against the fungi *C. albicans* and *A. niger* and compared with LL-37. The MIC values for each peptide are given in Table 4. P60.4-Ac showed a higher or equal activity against the Gram-negative strains *E. coli* and *P. aeruginosa* compared to LL-37. In some cases also bactericidal activity was determined for both peptides. P60.4-Ac showed an MIC at 6 µM against *C. albicans* and may well be fungicidal at 18 µM. P60.4Ac at 18 µM inhibited the germination of *A. niger* spores for 24 hours, whereas LL-37 shows no activity against *A. niger*.

EXAMPLE 8

Inhibition of Biofilm Formation

Compound P60.4Ac was prepared according to example 1 and tested for its effectiveness as inhibitor of *Pseudomonas putida* PCL1445 biofilm formation. A standard PVC biofilm assay was used, in which biofilms are formed on the polyvinyl chloride surface of the wells of microtiter plates. To the *P. putida* suspension in the wells, a solution of P60.4Ac (0.9 µM and 9 µM) was added and incubated for 10 hours. In result, it was found that P60.4Ac at 9 µM inhibited biofilm formation by more than 90%, whereas 0.9 µM resulted in a decrease of approx. 50% compared with buffer solution without the peptide.

EXAMPLE 9

Inhibition of Formed Biofilms

Compound P60.4Ac was prepared according to example 1 and tested for its effectiveness in disrupting *Pseudomonas putida* biofilms. The biofilms were formed using a standard PVC biofilm assay as in example 7. Biofilms were allowed to form in the wells of the microtiter plate from *P. putida*. PCL-1445 suspensions over 7 hours. After that, different quantities of P60.4Ac were added, as well as controles, i.e. DMSO and the buffered medium solution, M63, respectively. After 18 hours of incubation, the biofilms were assessed via their optical density at 595 nm (OD595). In result, DMSO resulted only in a small reduction of OD595 in comparison with M63, whereas P60.4Ac disrupted the biofilms substantially, depending on its concentration.

FIG. 1 shows the OD595 values for the various molar concentrations of P60.4Ac (bars 1 to 5), DMSO and M63.

TABLE 4

Antimicrobial activity of P60.4-Ac compared with LL-37

| Organism (strain) | Incubation time (h) | Peptide | MIC[a] (µM) |
|---|---|---|---|
| *E. coli* ATCC8739 | 24 | LL-37 | 3 |
|  |  | P60.4-Ac | 2 |
|  | 48 | LL-37 | 7[b] |
|  |  | P60.4-Ac | 3[c] |
| *P. aeruginosa* ATCC9027 | 24 | LL-37 | 3 |
|  |  | P60.4-Ac | 3 |
|  | 48 | LL-37 | 14[d] |
|  |  | P60.4-Ac | 6[b] |
| *C. albicans* ATCC10231 | 24 | LL-37 | 12 |
|  |  | P60.4-Ac | 6 |
|  | 48 | LL-37 | >18[e] |
|  |  | P60.4-Ac | 6[f] |
| *A. niger* ATCC14406 | 24 | LL-37 | >18 |
|  |  | P60.4-Ac | 18 |
|  | 48 | LL-37 | >18[e] |
|  |  | P60.4-Ac | >18[e] |

[a]MIC was defined as the lowest concentration of peptide that inhibited the bacterial visible growth after incubation for 24 or 48 hours at 37° C. Results given are mean values of three independent determinations.
[b]Bactericidal at 18 µM
[c]Bactericidal at 6 µM
[d]Bacteriostatic
[e]Recovery of viable organisms was not performed, as growth in all wells was clearly visible
[f]Possible fungicidal at 18 µM, fungistatic at 6 µM

The invention claimed is:

1. A pharmaceutical composition for treating a bacterial or fungal infection in a mammal that comprises the compound of formula (1) that comprises a core amino acid sequence: $X_1KEFX_2RIVX_3RIKX_4FLRX_5LVX_6$ (SEQ ID NO: 1), wherein X1 represents an N-terminal part;
X2 is K or E;
X3 is Q or E;
X4 is D or R;
X5 is N or E;
X6 represents a C-terminal part;
wherein one or more of the amino acids of the core amino acid sequence is optionally derivatized, and wherein
(a) the N-terminal part is acetylated, and/or
(b) the C-terminal part is amidated, and/or
(c) the core amino acid sequence is different from KEFKRIVQRIKDFLRNLV (SEQ ID NO:2),
along with one or more pharmaceutically acceptable carriers or excipients.

2. The composition of claim 1 which is adapted for parenteral administration.

3. The composition of claim 2 wherein the parenteral administration is intravascular, intramuscular, subcutaneous, or intralesional injection.

4. The composition of claim 1 which is adapted for the local administration to the mucosa of an affected region or tissue.

5. The composition of claim 4 wherein said composition is in the form of an irrigation liquid, ear drops, nose drops, an aerosol, a powder aerosol, a liquid for nebulization, a gel, a suspension, or a mucoadhesive dosage form.

6. The composition of claim 1 which further comprises a drug targeting agent, a bioavailability enhancing agent, and/or a controlled delivery agent.

7. The composition of claim 1 which further comprises at least one preservative, and wherein the content of the preservative is below the content needed effectively to preserve a corresponding placebo composition.

8. The composition of claim 1 which is substantially free of preservatives.

9. A method to exert an antimicrobial effect in the prophylactic or therapeutic treatment of a bacterial or fungal infection of a mammal, which method comprises administering to a mammal in need of such treatment an effective amount of a compound of formula (1) that comprises a core amino acid sequence: $X_1KEFX_2RIVX_3RIKX_4FLRX_5LVX_6$ (SEQ ID NO:1), wherein $X_1$ represents an N-terminal part;
$X_2$ is K or E;
$X_3$ is Q or E;
$X_4$ is D or R;
$X_5$ is N or E;
$X_6$ represents a C-terminal part;
wherein one or more of the amino acids of the core amino acid sequence is optionally derivatized, and wherein
(a) the N-terminal part is acetylated, and/or
(b) the C-terminal part is amidated, and/or
(c) the core amino acid sequence is different from KEFKRIVQRIKDFLRNLV (SEQ ID NO:2).

10. The method of claim 1, wherein the N-terminal part $X_1$ comprises the amino acids I and/or G.

11. The method of claim 1, wherein the C-terminal part $X_6$ comprises a sequence of at least 4 amino acids or amino acid derivatives.

12. The method of claim 11, wherein the C-terminal part $X_6$ comprises PRTE or RPLR, wherein one or more of the amino acids of said C-terminal part $X_6$ is optionally derivatized.

13. The method of claim 1, wherein the compound comprises a peptide with a sequence of 24 amino acids or derivatives thereof, said sequence being selected from
IGKEFKRIVQRIKDFLRNLVPRTE (SEQ ID NO:3) and
IGKEFKRIVERIKRFLRELVRPLR (SEQ ID NO:4), and
wherein one or more of the amino acids is optionally derivatized.

14. The method of claim 13, wherein the N-terminus is acetylated and the C-terminus is amidated.

15. The method of claim 1, wherein the bacterial or fungal infection is caused by planktonic microorganisms.

16. The method of claim 15, wherein the bacterial or fungal infection is an acute or chronic systemic infection.

17. The method of claim 15, wherein the systemic infection is associated with septic shock.

18. The method of claim 15, wherein the immune system of the mammal is suppressed through a disease or medication.

19. The method of claim 1, wherein the bacterial or fungal infection is caused by microorganisms capable of being sessile and forming biofilms.

20. The method of claim 1, wherein the bacterial or fungal infection is an acute or chronic local or regional infection.

21. The method of claim 20, wherein the local or regional infection is an infection of the lower or upper airways or the respiratory system or otitis media.

22. The method of claim 21 wherein the infection is otitis media, bronchitis, pneumonia, or sinusitis.

23. The method of claim 20, wherein the mammal suffers from cystic fibrosis.

24. The method of claim 20, wherein the immune system of the mammal is suppressed through a disease or medication.

25. The method of claim 20, wherein the local or regional infection is an infection of the liver, the spleen, the periodontium, an eye, a kidney, the skin, the vagina, the urethra, or the heart.

26. The method of claim 20, wherein the local or regional infection is associated with the implantation or insertion of a medical device into the mammal.

27. The method of claim 26 wherein the medical device is a heart valve, a venous catheter, a urinary catheter, a contact lens, a speech button, a tympanostomy tube, an intrauterine device, or an artificial bone.

28. The method of claim 1, which further comprises simultaneously administering to said mammal an additional antimicrobial or antifungal agent.

29. The method of claim 28, wherein the additional antimicrobial or antifungal agent is combined with the compound of formula (1) in a single medicament.

30. The method of claim 1, wherein the bacterial or fungal infection is not simultaneously treated with a medicament comprising an additional active ingredient.

* * * * *

SEQUENCE LISTING

```
<160> NUMBER OF SEQ ID NOS: 6

<210> SEQ ID NO 1
<211> LENGTH: 18
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 4
<223> OTHER INFORMATION: Xaa = Lys or Glu
<220> FEATURE:
<221> NAME/KEY: VARIANT
<222> LOCATION: 8
<223> OTHER INFORMATION: Xaa = Gln or Glu
<220> FEATURE:
<221> NAME/KEY: VARIANT
<222> LOCATION: 12
<223> OTHER INFORMATION: Xaa = Asp or Arg
<220> FEATURE:
<221> NAME/KEY: VARIANT
<222> LOCATION: 16
<223> OTHER INFORMATION: Xaa = Asn or Glu
```

<400> SEQUENCE: 1

Phe Glu Phe Xaa Arg Ile Val Xaa Arg Ile Lys Xaa Phe Leu Arg Xaa
1               5                   10                  15
Leu Val

<210> SEQ ID NO 2
<211> LENGTH: 18
<212> TYPE: PRT
<213> ORGANISM: Artificial Sequence
<220> FEATURE:
<223> OTHER INFORMATION: Synthetic construct

<400> SEQUENCE: 2

Phe Glu Phe Lys Arg Ile Val Gln Arg Ile Lys Asp Phe Leu Arg Asn
1               5                   10                  15
Leu Val

<210> SEQ ID NO 3
<211> LENGTH: 24
<212> TYPE: PRT
<213> ORGANISM: Artificial Sequence
<220> FEATURE:
<223> OTHER INFORMATION: Synthetic construct

<400> SEQUENCE: 3

Ile Gly Lys Glu Phe Lys Arg Ile Val Gln Arg Ile Lys Asp Phe Leu
1               5                   10                  15
Arg Asn Leu Val Pro Arg Thr Glu
            20

<210> SEQ ID NO 4
<211> LENGTH: 24
<212> TYPE: PRT
<213> ORGANISM: Artificial Sequence
<220> FEATURE:
<223> OTHER INFORMATION: Synthetic construct

<400> SEQUENCE: 4

Ile Gly Lys Glu Phe Lys Arg Ile Val Glu Arg Ile Lys Arg Phe Leu
1               5                   10                  15
Arg Glu Leu Val Arg Pro Leu Arg
            20

<210> SEQ ID NO 5
<211> LENGTH: 4
<212> TYPE: PRT
<213> ORGANISM: Artificial Sequence
<220> FEATURE:
<223> OTHER INFORMATION: Synthetic construct

<400> SEQUENCE: 5

Pro Arg Thr Glu
1

<210> SEQ ID NO 6
<211> LENGTH: 4
<212> TYPE: PRT
<213> ORGANISM: Artificial Sequence
<220> FEATURE:
<223> OTHER INFORMATION: Synthetic construct

```
<400> SEQUENCE: 6

Arg Pro Leu Arg
1
```